United States Patent [19]

Trudell

[11] Patent Number: 5,069,661
[45] Date of Patent: Dec. 3, 1991

[54] CIRCULATORY SUPPORT SYSTEM

[75] Inventor: Leonard A. Trudell, Warwick, R.I.

[73] Assignee: Brigham and Women's Hospital, Boston, Mass.

[21] Appl. No.: 195,594

[22] Filed: May 18, 1988

[51] Int. Cl.⁵ .............................................. A61M 37/00
[52] U.S. Cl. ............................................ 604/4; 604/26; 604/30; 128/DIG. 3
[58] Field of Search ................. 604/4, 30, 31, 65, 66, 604/67, 118, 26; 128/DIG. 3, DIG. 7

[56] References Cited

U.S. PATENT DOCUMENTS

| | | | |
|---|---|---|---|
| 3,017,885 | 1/1962 | Robicsek | 128/214 R |
| 4,466,804 | 8/1984 | Hino | 604/4 |
| 4,474,538 | 10/1984 | Schmid-Schönbein et al. | 417/53 |
| 4,540,399 | 9/1985 | Litzie et al. | 604/4 |
| 4,598,697 | 7/1986 | Numazawa et al. | 604/4 X |
| 4,610,656 | 9/1986 | Mortensen | 604/4 |
| 4,627,419 | 12/1986 | Hills | 604/4 X |
| 4,661,092 | 4/1987 | Popovich et al. | 604/26 |
| 4,698,207 | 10/1987 | Bringham et al. | 422/46 |
| 4,778,445 | 10/1988 | Hubbard et al. | 604/4 |

Primary Examiner—Robert A. Hafer
Assistant Examiner—Kerry Owens
Attorney, Agent, or Firm—Sterne, Kessler, Goldstein & Fox

[57] ABSTRACT

A low-pressure, low blood trauma hemodynamic support system is disclosed. The system may operate as a relatively static-volume, gravity-fed, extracorporeal blood circulation and oxygenation system that consists essentially of (1) a membrane-type blood oxygenator, (2) a non-occlusive roller pump, and (3) connecting tubes. The tubes connect the system components to create a compact system capable of supporting a patient in circulatory dysfunction who is to undergo a transplant operation, and is awaiting a donor organ.

21 Claims, 3 Drawing Sheets

CIRCULATORY SUPPORT SYSTEM

BACKGROUND OF THE INVENTION

1. Field of the Invention

The invention relates to systems for cardiopulmonary bypass, and more particularly to systems that provide hemodynamic and veno-arterial cardiopulmonary support.

2. Discussion of Related Art

Patients in circulatory dysfunction, for example, prospective organ transplant patients, often require a circulatory support system. In the case of a patient awaiting an organ transplant, such a system would be used as a "bridge-to-transplant"; that is, the system would be adapted to provide circulatory support until a donor organ could be obtained. As used in this specification, the term "bridge-to-transplant" generically refers to the function of providing circulatory assistance in the presence of cardiac dysfunction, or other circulatory dysfunction.

Typical cardiopulmonary bypass systems are rather complex, and generally are not particularly well-adapted for applications such as the "bridge-to-transplant." Moreover, most standard systems exhibit poor hemodynamic characteristics. That is, such systems typically cause too much damage to the blood to be useful for extended periods.

For example, typical cardiopulmonary bypass systems are disclosed in U.S. Pat. No. 3,890,969 to Fischel, U.S. Pat. No. 4,466,804 to Hino, and U.S. Pat. No. 4,610,656 to Mortensen. Such conventional systems commonly utilize several pumps, a venous reservoir, an arterial reservoir, and a separate bubble-trapping device.

These conventional systems exhibit several disadvantages. The most apparent disadvantage is the overall complexity of such systems. For example, the pumps may need to be synchronized with each other, or each of the reservoirs or bubble traps may need a special support frame. Also, the numerous components require extensive tubing and interconnections.

The complexity of the conventional systems leads to higher costs of manufacture and operation. Also, the more complex systems may take longer to set up, and system set-up may require expert personnel and supervision. Even with such expert personnel present, the system's complexity increases the risk of error in setting up the system. Likewise, once in operation, a conventional system requires continuous monitoring and adjustment by expert personnel.

Moreover, conventional cardiopulmonary bypass systems are not usable for long-term application because they significantly damage the blood after a fairly short use (e.g., 6–8 hours). For instance, conventional occlusive roller pumps mechanically destroy red blood cells, and centrifugal pumps expose blood elements to high shear forces, which also destroy red blood cells. This "blood trauma" can occur in any cardiopulmonary bypass system. It is caused and/or aggravated by occlusive or high-shear pumps, interconnections and other system components likely to increase system pressure or turbulence.

The above factors illustrate the desirability of a simple cardiopulmonary bypass system with relatively few components. Devices similar to that disclosed in U.S. Pat. No. 4,540,399 to Litzie et al. represent an attempt to achieve such simplicity. Litzie et al. disclose an emergency bypass system with one non-occlusive pump, an oxygenator, and a separate bubble trap. The Litzie patent specifies a centrifugal rotor-type pump connected proximal (i.e., on the venous side) to the oxygenator.

The Litzie et al. patent teaches a simplified cardiopulmonary bypass system compared to other known systems. However, the Litzie et al. system requires the bubble-trapping device in addition to the pump and oxygenator.

Also, the pump disclosed in Litzie et al. operates on the principle of high shear forces. As noted above, exposing the blood elements to these high shear forces cause significant damage to the blood.

The advent and increasing use of cardiac transplantation as a formal treatment has brought about the need for a circulatory support system capable of supporting a patient in circulatory dysfunction for some length of time until a donor organ can be obtained. Such a circulatory support system would also be quite useful in numerous other situations, such as (1) where the patient is in a state of cardiogenic shock; (2) where the patient is in a state of septic shock, (3) for postcardiotomy weaning from the bypass; and (4) for assisting the circulatory system to avoid an impending myocardial infarction. It is highly desirable to simplify the system as much as possible.

SUMMARY OF THE INVENTION

The present invention provides a greatly simplified cardiopulmonary bypass system. The system of the present invention can be implemented using only two basic components (a pump and an oxygenator), along with the requisite tubes, connectors, and cannulations. The components are connected as a closed series circuit adapted for extracorporeal processing of the patient's blood.

To eliminate the need for separate reservoirs, the oxygenator means of the present invention may be provided with sufficient flow-through capacity in excess of normal system flow rates that the oxygenator functions as its own reservoir In this regard, the system of the present invention is a relatively static-volume system as compared to conventional systems, which normally include one or more separate reservoirs or the like. The oxygenator may also be equipped with an integral housing, gas heater and thermal insulation. Thus, the oxygenator may also eliminate the need for a heat exchanger to maintain fluid temperature.

To eliminate the need for a separate bubble trap, the pump itself may be oriented so as to function as its own trap for air bubbles.

The pump and oxygenator may be positioned such that the fluid may flow through the oxygenator to the inlet of the pump by gravity, or by gravity and the patient's venous pressure. This orientation further enables a smooth and low-pressure fluid flow through the system, further reducing blood trauma.

The system of the present invention can provide partial veno-arterial cardiopulmonary support over a relatively long period (i.e., one to ten days) because of its very low overall pressure and blood trauma characteristics. The system is capable not only of providing cardiopulmonary support but also of providing hemodynamic support over a potentially long period. The system of the present invention is particularly adapted for "bridge-to-transplant" hemodynamic support (for example, the system can assist the natural heart in maintaining adequate blood circulation, using a counterpulsation mode, while a transplant patient awaits a donor organ).

The system is, however, able to achieve a number of objectives in a variety of situations involving circulatory dysfunction. The system of the present invention can assist circulation during relatively mild circulatory dysfunction, and also can provide acute assistance during severe refractory cardiac failure caused by myocardial infarction, cardiomyopathy, or post-cardiac surgery. The system of the present invention is useful to provide perioperative support and stabilization of high-risk patients, such as coronary bypass surgery patients.

The low-trauma, low-pressure system of the present invention contributes desirable overall hemodynamic characteristics. Many of the features of the present invention that improve the overall hemodynamics of the system also help to simplify the system, and to make it more reliable and compact.

The small number of system components also enables easier set-up and operation, and reduces the risk of system malfunction. To further reduce the risk of system malfunction, the system may be equipped with various fail-safe features. Such equipment monitors and controls various pressures and flow rates to ensure proper operation. Although the system of the present invention may require periodic monitoring and adjustment by expert personnel during operation, it is relatively automatic. That is, compared to conventional systems, which tend to be more complex, the system of the present invention requires much less monitoring and adjustment during operation.

The system of the present invention also causes less damage to the blood than conventional systems, making the system of the present invention more suitable for long-term applications. Trauma to the patient's blood is reduced principally by the simplicity of the blood circuit, especially the low number of circuit elements, the non-occlusive pump and the design of the oxygenator. In addition, overall trauma to the patient is reduced. The present invention reduces extracorporeal processing of the blood compared to conventional bypass systems and procedures. The absence of separate fluid reservoirs reduces the fluid volume of the system of the present invention. Because less of the patient's blood is withdrawn from the body at one time, the overall trauma to the patient is reduced.

DETAILED DESCRIPTION OF THE PREFERRED EMBODIMENTS

The system of the present invention is suitable for many uses, specifically including hemodynamic "bridge-to-transplant" support. As noted in the "Background" section, "bridge-to-transplant" refers generally to circulatory assistance in the presence of circulatory dysfunction, and is not limited to situations involving organ transplant.

The disclosed system is useful for providing circulatory assistance in a variety of situations; adapting the disclosed system for some uses may require minor adjustments that will be readily apparent to those skilled in the art. At least the following situations in which the disclosed system will be useful are envisioned: balloon angioplasty; pre- and/or postcoronary bypass support, including assistance in weaning patient from total heart-lung support; support during and after myocardial infarction, including right, left, or biventricular heart failure; assistance during pulmonary edema (a clinical state caused by valvular dysfunction); assistance during hemorrhagic shock and septic shock; and during patient transport.

Figure 1:
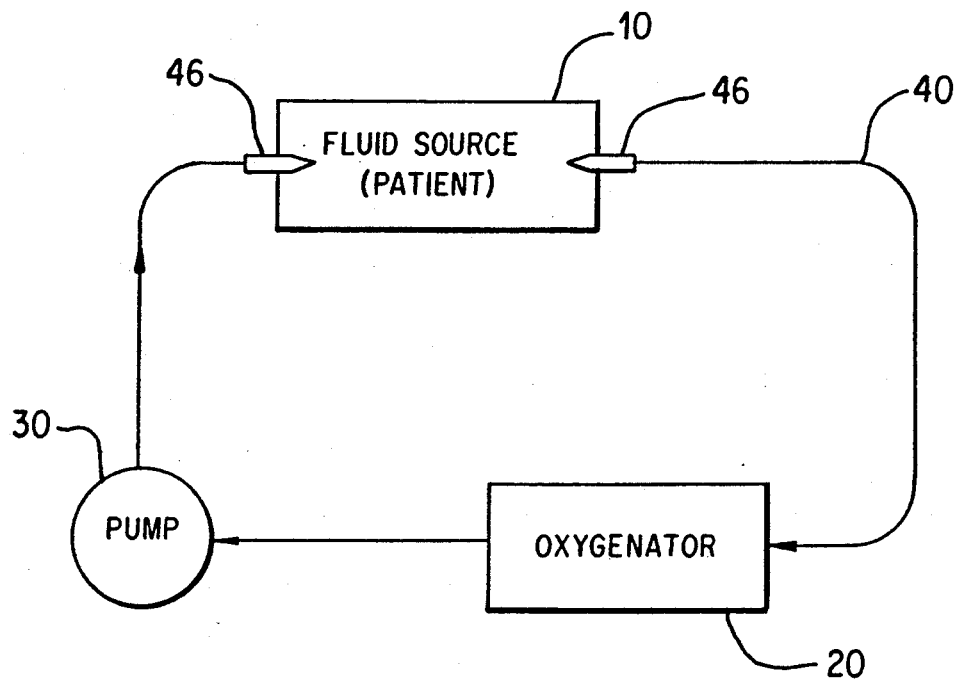
FIG. 1 is a block diagram depicting the preferred configuration of the system of the present invention.
Figure 2:
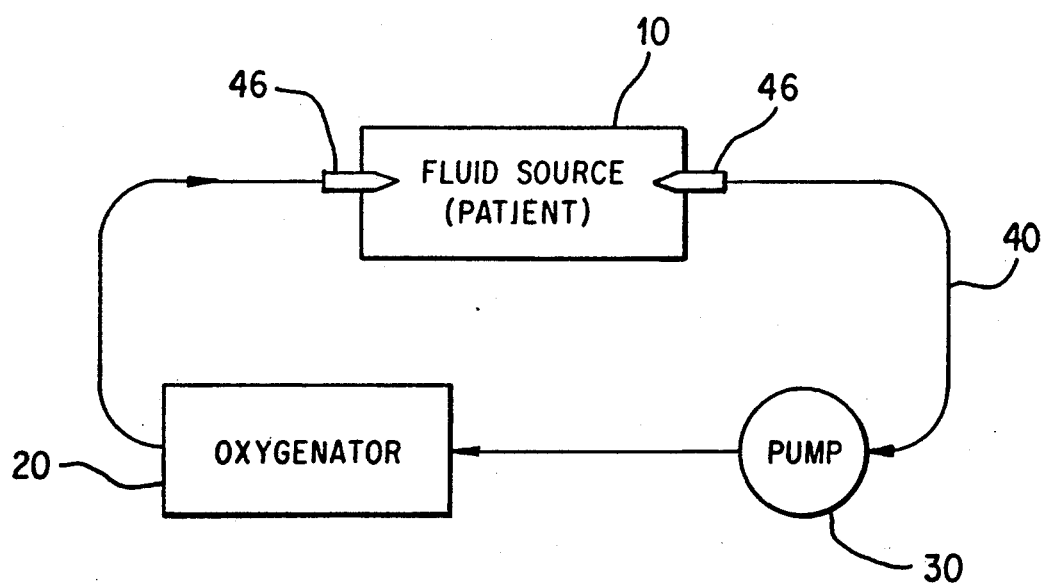
FIG. 2 is a block diagram depicting an alternative configuration of the system of the present invention.

Referring to FIGS. 1 and 2, the "bridge-to-transplant" system of the present invention is a relatively static-volume, gravity-fed, extracorporeal blood circulation and oxygenation system. The system consists essentially of an oxygenator 20, a pump 30, and connecting tubes 40. Because the entire system can be implemented with so few basic components, the system is extremely compact.

The system also includes first and second cannulations 46. The cannulations 46 are a conventional means of drawing blood from and returning blood to the patient in conjunction with an extracorporeal blood treatment system.

As shown by FIGS. 1 and 2, the bridge-to-transplant system may be configured to accommodate flow through the oxygenator to the pump (FIG. 1), or through the pump to the oxygenator (FIG. 2). Certain advantages of the present invention can be realized with either configuration, although the configuration shown in FIG. 1 is presently preferred.

For instance, the oxygenating means 20 may have sufficient flow-through capacity in excess of the normal flow through the system that the oxygenator functions as its own reservoir. This applies to various types of oxygenators, including hollow-fiber units. Utilizing an oxygenating means that includes the presently preferred planar-type oxygenator membrane 22, depicted in FIG. 3, in a "bridge-to-transplant" mode allows for fluctuation in the blood layer thickness and oxygenator volume because the flow is well below the oxygenator's designed capacity. The system achieves optimum performance when the rated flow-through capacity of the oxygenator is approximately three times normal system flow; that is, when the oxygenator is operated at approximately onethird of its rated flow. The normal flow rate for the bridge-to-transplant system ranges from approximately 1½ to 2¼ liters/minute. The flow rate varies with the size of the patient.

The principal criteria for the oxygenator 20 are its low-pressure, through-flow characteristics. The oxygenator should offer very low resistance to fluid (blood) flow. Flat-sheet membrane-type oxygenators best satisfy these criteria. The best results have been achieved using the Sarns-3M Travenol TMO, which features a fan-folded, interdigitated, porous membrane made of porous polypropylene.

Figure 3:
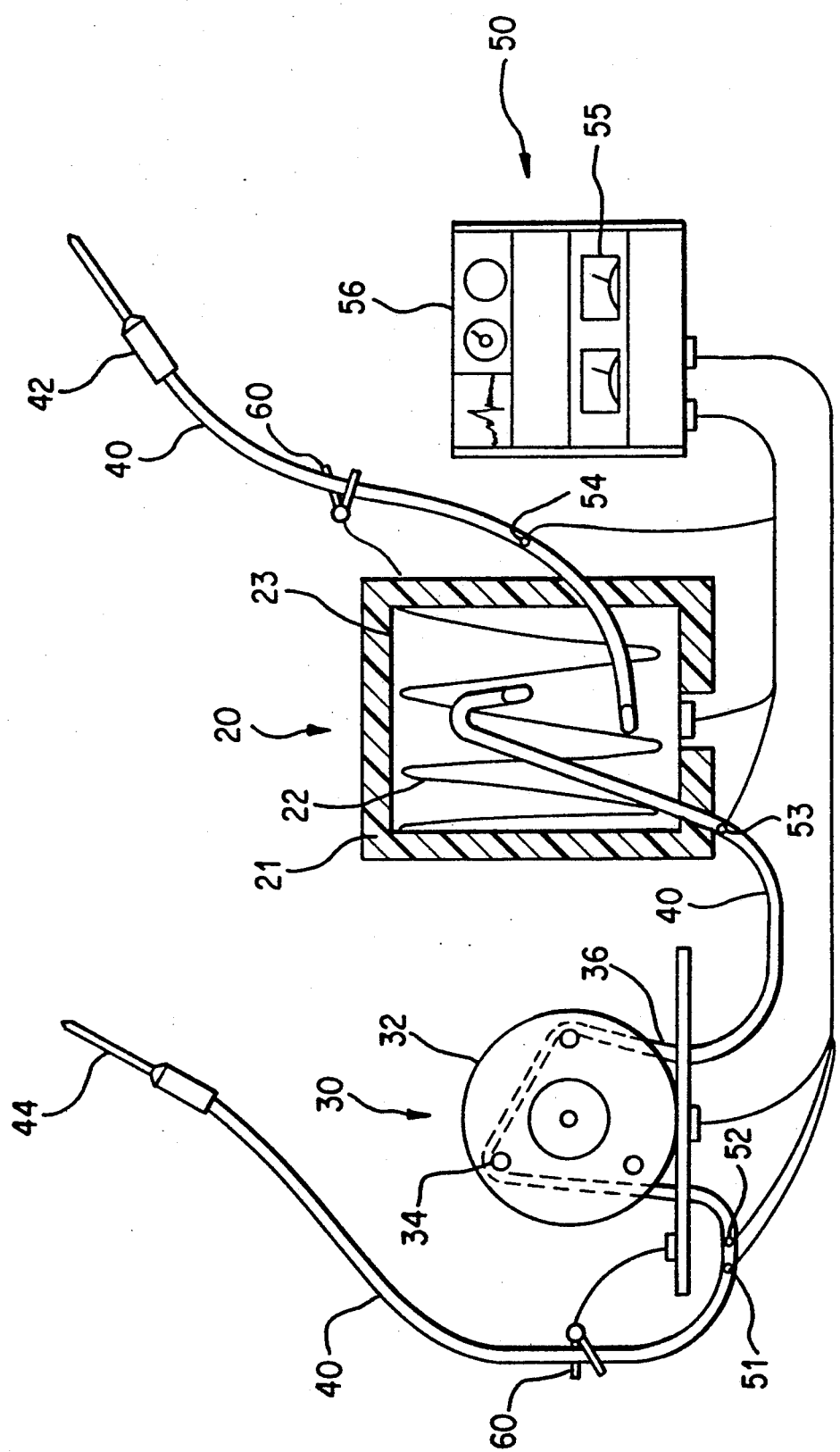
FIG. 3 is a schematic diagram of the preferred embodiment of the present invention.

The oxygenator may utilize a gas heater, as is conventional, and additionally may be equipped with an insulated housing to more efficiently maintain the proper blood temperature. The insulation 21 is depicted in FIG. 3, and may be any conventional thermally insulative material, such as polystyrene. In some conventional oxygenators, the gas heater and housing are integral with the oxygenator device. The Travenol TMO, for instance, fits into and is supported by a holder, or housing, that is equipped with an inlet gas heater. The TMO is a one-use disposable oxygenator whereas the housing is relatively permanent, so it is more practical to insulate the housing rather than the oxygenator itself. Similarly, if the bridge-to-transplant system utilizes a different type of oxygenator, such as a low pressure-gradient hollow fiber device, it is equally practical to insulate the oxygenator.

Most conventional oxygenators have an integral heat exchanger with sufficient capacity to allow hypothermic acute procedures. The standard TMO system ordinarily is equipped with a heat exchanger adjacent to the oxygenator. The bridge-to-transplant system does not need as much heat exchange capacity because the support procedures are conducted at normothermia, with the blood temperature at approximately 98.6° F. Accordingly, the heat exchanger is excluded from the blood circuit, and the oxygenator housing is insulated.

Preliminary experiments have shown that when the housing for the Travenol TMO is insulated, the integral gas heater is sufficient to heat the entire oxygenator, with only a 1° C. drop in blood temperature through the entire circuit. Thus, in a preferred embodiment, to obviate the need for a separate heat exchanger, the TMO oxygenator includes an integral housing and gas heater, and, in accordance with the invention, the housing is thermally insulated The pump 30 includes the pump disk 32, rollers 34, and pump tube 36. The pump tube 36 is wrapped over the top of the disk 32, forming an inverted "U" shape. As the disk turns, the rollers 34 "massage" the tube 36, thereby moving blood through the tube.

The orientation of the pump 30 is another feature of the present invention. To eliminate the need for a separate bubble trap, the pump may be oriented so as to function as a trap for air bubbles in the fluid (blood). One method of integrating the "bubble trapping" function into pump 30 can be described with reference to FIGS. 3, 4, and 5. As shown, the pump 30 is a non-occlusive roller pump. The roller pump is positioned with its roller disk 32 nearly vertical; however, the pump will function as its own bubble trap whenever the middle portion of the pump tube (the portion that wraps around the pump disc) is higher than the pump inlet and outlet. The position of roller disk 32 allows the pump tube 36 to act as its own bubble trap. As shown in FIG. 5, any bubble emboli 46 will be caught and held in the highest point of the pump tube 36.

To further reduce blood trauma, flow through the bridge-to-transplant system should depend upon gravity drainage from the patient to the system components, not on suction from the pump 30. Accordingly, the pump 30 preferably is a non-occlusive roller pump that is substantially incapable of generating a negative inlet pressure (i.e., substantially incapable of suction).

Figure 4:
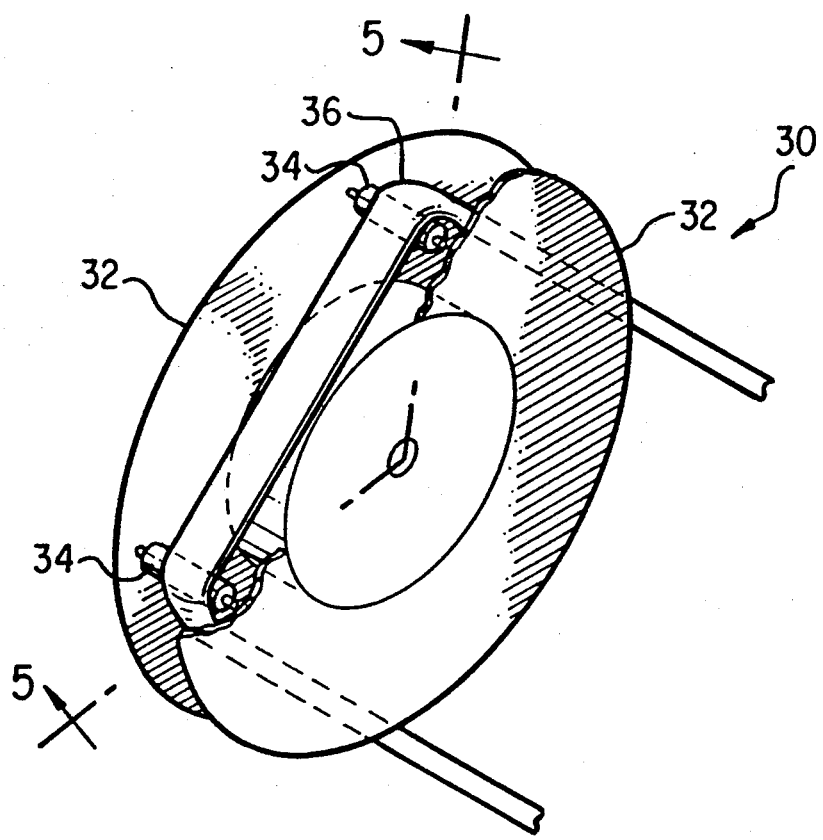
FIG. 4 is a detailed view of the pump shown in FIG. 3.
Figure 5:
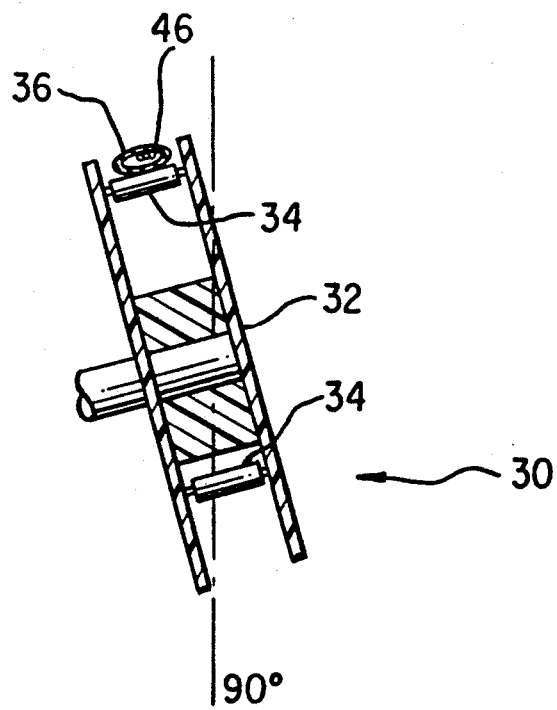
FIG. 5 is a sectional view of the pump of FIG. 3 depicting the pump's orientation to function as a bubble trap.

The roller pump preferably employs a flat-profiled pump tube, as shown in FIGS. 4 and 5. In this manner, the pump tube collapses in the absence of inlet pressure, and therefore the pump output ceases in the absence of "pre-load," or free flow from the preceding system component. These characteristics are further enhanced when the pump tube 36 is elastic; that is, the tube may be made of an elastic material such as a silicone elastomer, for example.

Optimum results have been achieved using the RhonePoulenc RP-06 pump. Although FIGS. 4 and 5 depict a pump with one disc and one tube, the RP-06 pump was designed with two stacked discs to hold two pump tubes for total cardiopulmonary bypass. The venous tube has a round cross-sectional profile, and the arterial tube has a flat cross-sectional profile. The pump is conventionally used to perfuse an oxygenator interposed between the venous and arterial pump tubes. In the bridge-to-transplant configuration, however, only the arterial tube is used. Using only the flat-profiled, arterial pump tube, the pump's output is dependent upon gravity flow or venous pressure to "pre-load" the inlet side of the pump. Should gravity drainage from the patient cease for any reason, the pump output will likewise cease, even if the pump continues to rotate. The flat-profiled tube does not allow the pump to develop negative inlet pressure.

A further advantage can be achieved by positioning the pump and oxygenator such that the blood may also flow through the oxygenator to the inlet of the pump by gravity (FIG. 1). Preferably, the system is situated below the patient's heart level. In this configuration, gravity drainage (hydrostatic pressure head) is the dominant "pre-load" mechanism, and the system pressure is maintained below 100 mmHg. Although the preferred range of system pressure is 40-100 mmHg, the system is operable over virtually any practicable range.

As illustrated by the above description, the bridge-to-transplant system may include a pump that acts as its own bubble trap, and an oxygenator that acts as its own reservoir and heat exchanger. Therefore, the entire system is very compact and simple. Additionally, the unique orientation and low number of the components results in a low-pressure, low blood trauma system that is particularly applicable to provide highly effective hemodynamic support and partial veno-arterial cardiopulmonary support over a potentially long period (one to seven days).

The simplicity of the system enhances its reliability. To further enhance reliability, the system may include measurement apparatus, fail-safe apparatus, and remote control and readout features. A clinical version of the system is depicted in FIG. 3, which includes the cannulations 42 and 44, the oxygenator 20, the pump 30, interconnecting tubes 40, and the measurement, failsafe, and remote control and readout device 50.

Various measurement devices may be included, such as flow-probe 51 and flow pressure transducers 52, 53 and 54. The flowmeter 55, which may be, for example, a conventional flowmeter such as those marketed by Carolina Medical Electronics Company, detects the pump outlet flow rate. Perfusion pressure transducer 52, which may be a conventional transducer such as the Hewlett-Packard Physiologic Monitor, detects the pump outlet pressure. Flow pressure transducers 53 and 54 operate to detect oxygenator fluid flow pressure. Transducers 53 and 54 may measure either oxygenator fluid inlet pressure or outlet pressure. As shown in FIG. 3, the system is adapted for flow through the oxygenator to the pump. Therefore, as shown in FIG. 3, transducer 54 corresponds to the oxygenator fluid inlet pressure, and transducer 53 corresponds to the oxygenator fluid outlet pressure These pressure transducers and flow-probes are conventional, well-known devices that produce a signal corresponding to the flow rate or pressure being monitored.

Also, the oxygenator may include means to regulate its inlet gas pressure comprising an inlet gas pressure transducer electronically interlocked to a servo-mechanism that controls the oxygenator ventilation gas outlet rate. The electronic interlock provides that the servo-mechanism adjusts its position in accordance with the signal from the transducer. This electronic interlock technique is fairly common, and well-known to those of ordinary skill in the art.

Alternatively, gas pressure can be regulated by means of a simple manometer and water seal. The seal is set at the desired pressure. If the gas pressure exceeds this pressure, the seal will open and allow the gas to bubble up through the water and escape through the seal.

The oxygenator is conventionally equipped with a shim, which is basically a "gas bag" that inflates to compress the fan-folded membrane, thereby ensuring that the blood layer in contact with the membrane is kept very thin. The shim may be equipped with a shim pressure transducer. The transducer is electronically interlocked to a servo-mechanism control of the shim pressure regulator.

Another feature that may be included is the pump speed control-counterpulsation apparatus. This apparatus operates to detect the patient's heartbeat, and to time pump output pulses accordingly. The RP-06 pump will be equipped as a counterpulsation apparatus.

The counterpulsation apparatus works in conjunction with electrocardiogram 56. The electrocardiogram supplies a signal corresponding to the patient's heartbeat as an input to a timing means. The timing means controls the pump's output pulses and pump speed in accordance with the signal from the electrocardiogram to ensure that pump output pulses occur at a rate compatible with the patient's circuloatory rate, and only during the natural heart's diastole (that is, during aortic valve closure). In the presently preferred embodiment, the timing means functions in a manner analogous to the timing circuitry included in conjunction with conventional aortic balloon pumps, such as those marketed by Datascope.

Also, the system may be equipped with fail-safe isolation clamps 60. The clamps automatically close if the pump stops turning, there isolating the system. This feature prevents the system from depleting a patient's blood supply in the event of pump stoppage.

The foregoing embodiments are representations of the present invention, and the full extent of the present invention is defined only by the claims.

What is claimed is:

1. A fluid circulation and oxygenation system, comprising:
   a first cannulation;
   means for oxygenating a fluid circulating in said system, connected to said first cannulation;
   a pump, connected to said oxygenating means, said pump including a pump tube that is positioned higher than an inlet and an outlet of said pump to thereby trap air bubbles in the fluid; and
   a second cannulation, connected to said pump.

2. The system of claim 1, wherein:
   said pump is substantially incapable of generating a negative inlet pressure.

3. The system of claim 1, wherein:
   said pump is a non-occlusive roller pump employing a flat-profiled, elastic pump tube.

4. The system of claim 1, wherein said oxygenator further comprises:
   an integral housing and gas heater; and
   thermal insulating means, operative to thermally insulate said integral housing and gas heater.

5. The system of claim 1, further comprising:
   counterpulsation means, said counterpulsation means being operative to detect the patient's heartbeat and to time pump output pulses accordingly.

6. The system of claim 1, further comprising:
   an electrocardiogram, said electrocardiogram being operative to produce a signal corresponding to a patient's heartbeat; and
   timing means, said timing means being operative to control said pump's output pulses in accordance with the signal from said electrocardiogram.

7. The system of claim 1, further comprising:
   perfusion pressure transducer means, said means being operative to produce a signal corresponding to pump outlet pressure.

8. The system of claim 1, further comprising:
   a flow-probe, said flow-probe being operative to produce a signal corresponding to pump outlet flow rate.

9. A fluid circulation and oxygenation system, comprising:
   a first cannulation;
   means for oxygenating a fluid circulating in said system, connected to said first cannulation;
   a non-occlusive, pulsatile pump, connected to said oxygenating means;
   means for sensing when the heart of said patient is being which indicates when the aortic valve of the heart is open and closed;
   means for causing said pump to operate in a counterpulsation fashion to pump said fluid only when said aortic valve is closed; and
   a second cannulation, connected to an outlet of said pump.

10. The system of claim 9, wherein:
    said oxygenating means is a flat-sheet membrane-type oxygenator.

11. The system of claim 10, wherein:
    said oxygenator employs a fan-folded, interdigitated, porous flat-sheet membrane.

12. The system of claim 9, wherein:
    the rated flow-through capacity of said oxygenating means is approximately three times normal system flow.

13. The system of claim 9, further comprising:
    pressure transducer means, said pressure transducer means being operative to produce a signal corresponding to the fluid inlet pressure of said oxygenating means.

14. The system of claim 9, further comprising:
    pressure transducer means, said pressure transducer means being operative to produce a signal corresponding to the fluid outlet pressure of said oxygenating means.

15. The system of claim 9, further comprising:
    gas pressure regulator means, said gas pressure regulator means being operative to regulate inlet gas pressure to said oxygenating means.

16. The system of claim 9, further comprising:
    inlet gas pressure transducer means, said inlet gas pressure transducer means being operative to produce a signal corresponding to gas pressure into said oxygenating means; and
    a servo-mechanism, said servo-mechanism being operative to adjust the oxygenator ventilation rate in accordance with the signal from said inlet gas pressure transducer.

17. The system of claim 9, further comprising:

shim pressure transducer means, said shim pressure transducer means being operative to produce a signal corresponding to shim pressure; and a servo-mechanism, said servo-mechanism being operative to adjust the shim pressure in accordance with the signal from said shim pressure transducer means.

18. An extracorporeal blood circulation and oxygenation system, comprising:

a venous cannulation through which blood may be drawn from a patient;

oxygenating means connected to said venous cannulation for oxygenating blood flowing through said system, said oxygenating means having sufficient flow-through capacity in excess of the flow from said venous cannulation that said oxygenating means functions as its own venous reservoir;

a non-occlusive, pulsatile pump, connected to said oxygenating means;

means for causing said pump to operate in a counter-pulsation fashion; and an arterial cannulation, connected to said pump, through which blood may be returned by said pump to a patient.

19. An extracorporeal blood circulation and oxygenation system, comprising:

a venous cannulation through which blood may be drawn from a patient;

a non-occlusive, pulsatile pump, connected to said venous cannulation;

means for causing said pump to operate in a counter-pulsation fashion;

means for oxygenating blood, connected to said pump, said oxygenating means having sufficient flow-through capacity in excess of the flow from said pump that said oxygenating means functions as its own venous reservoir; and an arterial cannulation, connected to said oxygenating means, through which blood may be returned by said pump to a patient.

20. An extracorporeal blood circulation and oxygenation system, comprising:

a venous cannulation through which blood may be drawn from a patient;

oxygenating means connected to said venous cannulation for oxygenating blood flowing through said system;

a non-occlusive, pulsatile pump, connected to said oxygenating means;

means for sensing when the heart of said patient is beating which indicates when the aortic valve of the heart is open and closed;

means for causing said pump to operate in a counter-pulsation fashion to pump blood only when said aortic valve is closed; and an arterial cannulation, connected to said pump, through which blood may be returned by said pump to said patient.

21. A blood circulation and oxygenation system, having a fluid circulation path consisting essentially of:

a first cannulation;

means for oxygenating blood circulating in said system, connected to said first cannulation;

a non-occlusive, pulsatile pump, connected to said oxygenating means; including means for causing said pump to operate in a counter-pulsation fashion and a second cannulation, connected to an outlet of said pump.

* * * * *